United States Patent
Kleine et al.

(10) Patent No.: US 9,561,351 B2
(45) Date of Patent: Feb. 7, 2017

(54) DRUG DELIVERY SPIRAL COIL CONSTRUCT

(75) Inventors: Klaus Kleine, Los Gatos, CA (US);
David C. Gale, San Jose, CA (US);
Fozan El-Nounou, Santa Clara, CA (US); Syed F. A. Hossainy, Fremont, CA (US); Florian Ludwig, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1199 days.

(21) Appl. No.: 11/445,079

(22) Filed: May 31, 2006

(65) Prior Publication Data
US 2007/0282425 A1 Dec. 6, 2007

(51) Int. Cl.
*A61M 31/00* (2006.01)
*A61F 2/88* (2006.01)

(52) U.S. Cl.
CPC .............. *A61M 31/002* (2013.01); *A61F 2/88* (2013.01); *A61F 2/885* (2013.01); *A61F 2250/0039* (2013.01); *A61F 2250/0067* (2013.01)

(58) Field of Classification Search
CPC ................ A61F 2/94; A61F 2/95; A61F 2/88; A61F 2/885; A61F 2250/0067; A61F 2250/0039; A61M 31/002
USPC .................. 623/1.22, 1.15, 1.16, 1.42–1.48, 623/1.39–1.41, 1.2; 604/507, 508, 523, 604/528; 606/194, 200, 195
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,773,737 A | 11/1973 | Goodman et al. | |
| 3,849,514 A | 11/1974 | Gray, Jr. et al. | |
| 3,892,238 A | 7/1975 | Banford et al. | |
| 4,226,243 A | 10/1980 | Shalaby et al. | |
| 4,329,383 A | 5/1982 | Joh | |
| 4,343,931 A | 8/1982 | Barrows | |
| 4,529,792 A | 7/1985 | Barrows | |
| 4,611,051 A | 9/1986 | Hayes et al. | |
| 4,649,922 A * | 3/1987 | Wiktor | 606/194 |
| 4,656,242 A | 4/1987 | Swan et al. | |

(Continued)

FOREIGN PATENT DOCUMENTS

| | | |
|---|---|---|
| DE | 42 24 401 | 1/1994 |
| DE | 2001-190687 | 7/2001 |

(Continued)

OTHER PUBLICATIONS

Anonymous, *Cardiologists Draw—Up the Dream Stent*, Clinica 710:15 (Jun. 17, 1996), http://www.dialociweb.com/cgi/document?req=1061848202959, printed Aug. 25, 2003 (2 pages).

(Continued)

*Primary Examiner* — Jocelin Tanner
(74) *Attorney, Agent, or Firm* — Squire Patton Boggs (US) LLP

(57) ABSTRACT

An implantable medical device is disclosed having a helical construct including a set of spiral coils for local in vivo application of a therapeutic substance in a biological lumen. The helical construct is configured to apply less than 0.75 Bar of pressure to the biological lumen wall. The helical construct can have at least two sets of spiral coils having opposing helical directions. The device can be used for the treatment of vascular disorders such as restenosis and vulnerable plaque.

49 Claims, 2 Drawing Sheets

(56) References Cited

U.S. PATENT DOCUMENTS

| | | |
|---|---|---|
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,554,114 A * | 9/1996 | Wallace et al. ............... 604/508 |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,749,919 A * | 5/1998 | Blanc ........................ 623/1.22 |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,063,111 A * | 5/2000 | Hieshima et al. ........... 623/1.22 |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,146,417 A * | 11/2000 | Ischinger ................... 623/1.15 |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |

(56) References Cited

U.S. PATENT DOCUMENTS

| | | | |
|---|---|---|---|
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,423,092 B2* | 7/2002 | Datta et al. | 623/1.15 |
| 6,451,373 B1 | 9/2002 | Hossainy et al. | |
| 6,458,092 B1* | 10/2002 | Gambale et al. | 604/22 |
| 6,475,779 B2 | 11/2002 | Mathiowitz et al. | |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,610,086 B1* | 8/2003 | Kock et al. | 623/1.22 |
| 6,613,432 B2 | 9/2003 | Zamora et al. | |
| 6,616,765 B1 | 9/2003 | Hossanony et al. | |
| 6,620,617 B2 | 9/2003 | Mathiowitz et al. | |
| 6,623,448 B2 | 9/2003 | Slater | |
| 6,625,486 B2 | 9/2003 | Lundkvist et al. | |
| 6,641,611 B2 | 11/2003 | Jayaraman | |
| 6,645,135 B1 | 11/2003 | Bhat | |
| 6,645,195 B1 | 11/2003 | Bhat et al. | |
| 6,645,237 B2* | 11/2003 | Klumb et al. | 623/1.11 |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,689,350 B2 | 2/2004 | Uhrich | |
| 6,695,920 B1 | 2/2004 | Pacetti et al. | |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,730,064 B2 | 5/2004 | Ragheb et al. | |
| 6,733,536 B1* | 5/2004 | Gellman | 623/23.66 |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,746,773 B2 | 6/2004 | Llanos et al. | |
| 6,749,626 B1 | 6/2004 | Bhat et al. | |
| 6,753,071 B1 | 6/2004 | Pacetti et al. | |
| 6,758,859 B1 | 7/2004 | Dang et al. | |
| 6,759,054 B2 | 7/2004 | Chen et al. | |
| 6,764,505 B1 | 7/2004 | Hossainy et al. | |
| 6,776,796 B2 | 8/2004 | Falotico et al. | |
| 6,780,424 B2 | 8/2004 | Claude | |
| 6,783,793 B1* | 8/2004 | Hossainy et al. | 427/2.25 |
| 6,790,228 B2 | 9/2004 | Hossainy et al. | |
| 6,808,533 B1* | 10/2004 | Goodwin et al. | 623/1.13 |
| 6,824,559 B2 | 11/2004 | Michal | |
| 6,861,088 B2 | 3/2005 | Weber et al. | |
| 6,865,810 B2 | 3/2005 | Stinson | |
| 6,869,443 B2 | 3/2005 | Buscemi et al. | |
| 6,878,160 B2 | 4/2005 | Gilligan et al. | |
| 6,887,270 B2 | 5/2005 | Miller et al. | |
| 6,887,485 B2 | 5/2005 | Fitzhugh et al. | |
| 6,890,546 B2 | 5/2005 | Mollison et al. | |
| 6,890,583 B2 | 5/2005 | Chudzik et al. | |
| 6,899,731 B2 | 5/2005 | Li et al. | |
| 6,939,374 B2* | 9/2005 | Banik et al. | 623/1.27 |
| 6,974,473 B2* | 12/2005 | Barclay et al. | 623/1.22 |
| 7,008,667 B2 | 3/2006 | Chudzik et al. | |
| 7,229,471 B2* | 6/2007 | Gale et al. | 623/1.15 |
| 7,255,710 B2* | 8/2007 | White et al. | 623/1.15 |
| 2001/0007083 A1 | 7/2001 | Roorda | |
| 2001/0029351 A1 | 10/2001 | Falotico et al. | |
| 2001/0037145 A1 | 11/2001 | Guruwaiya et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0051730 A1 | 5/2002 | Bodnar et al. | |
| 2002/0077693 A1* | 6/2002 | Barclay et al. | 623/1.13 |
| 2002/0082679 A1 | 6/2002 | Sirhan et al. | |
| 2002/0087123 A1 | 7/2002 | Hossainy et al. | |
| 2002/0091433 A1 | 7/2002 | Ding et al. | |
| 2002/0111590 A1 | 8/2002 | Davila et al. | |
| 2002/0165608 A1 | 11/2002 | Llanos et al. | |
| 2002/0176849 A1 | 11/2002 | Slepian | |
| 2002/0183581 A1 | 12/2002 | Yoe et al. | |
| 2002/0188037 A1 | 12/2002 | Chudzik et al. | |
| 2002/0188277 A1 | 12/2002 | Roorda et al. | |
| 2003/0004141 A1 | 1/2003 | Brown | |
| 2003/0028243 A1 | 2/2003 | Bates et al. | |
| 2003/0028244 A1 | 2/2003 | Bates et al. | |
| 2003/0028245 A1 | 2/2003 | Barclay et al. | |
| 2003/0032767 A1 | 2/2003 | Tada et al. | |
| 2003/0033007 A1* | 2/2003 | Sirhan et al. | 623/1.42 |
| 2003/0036794 A1 | 2/2003 | Ragheb et al. | |
| 2003/0039689 A1 | 2/2003 | Chen et al. | |
| 2003/0040790 A1 | 2/2003 | Furst | |
| 2003/0059520 A1 | 3/2003 | Chen et al. | |
| 2003/0060877 A1* | 3/2003 | Falotico et al. | 623/1.42 |
| 2003/0065377 A1 | 4/2003 | Davila et al. | |
| 2003/0072868 A1 | 4/2003 | Harish et al. | |
| 2003/0073961 A1 | 4/2003 | Happ | |
| 2003/0083646 A1 | 5/2003 | Sirhan et al. | |
| 2003/0083739 A1 | 5/2003 | Cafferata | |
| 2003/0097088 A1 | 5/2003 | Pacetti | |
| 2003/0097173 A1 | 5/2003 | Dutta | |
| 2003/0099712 A1 | 5/2003 | Jayaraman | |
| 2003/0105518 A1 | 6/2003 | Dutta | |
| 2003/0113439 A1 | 6/2003 | Pacetti et al. | |
| 2003/0125800 A1* | 7/2003 | Shulze et al. | 623/1.15 |
| 2003/0135255 A1* | 7/2003 | Sundar | 623/1.11 |
| 2003/0150380 A1 | 8/2003 | Yoe | |
| 2003/0157241 A1 | 8/2003 | Hossainy et al. | |
| 2003/0158517 A1 | 8/2003 | Kokish | |
| 2003/0190406 A1 | 10/2003 | Hossainy et al. | |
| 2003/0207020 A1 | 11/2003 | Villareal | |
| 2003/0211230 A1 | 11/2003 | Pacetti et al. | |
| 2004/0018296 A1 | 1/2004 | Castro et al. | |
| 2004/0029952 A1 | 2/2004 | Chen et al. | |
| 2004/0034405 A1* | 2/2004 | Dickson | 623/1.11 |
| 2004/0047978 A1 | 3/2004 | Hossainy et al. | |
| 2004/0047980 A1 | 3/2004 | Pacetti et al. | |
| 2004/0052858 A1 | 3/2004 | Wu et al. | |
| 2004/0052859 A1* | 3/2004 | Wu et al. | 424/490 |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072922 A1 | 4/2004 | Hossainy et al. | |
| 2004/0073298 A1 | 4/2004 | Hossainy | |
| 2004/0086542 A1 | 5/2004 | Hossainy et al. | |
| 2004/0086550 A1 | 5/2004 | Roorda et al. | |
| 2004/0096504 A1 | 5/2004 | Michal | |

(56) References Cited

U.S. PATENT DOCUMENTS

| | | | |
|---|---|---|---|
| 2004/0098117 A1 | 5/2004 | Hossainy et al. | |
| 2004/0117006 A1* | 6/2004 | Lewis et al. | 623/1.42 |
| 2004/0215336 A1* | 10/2004 | Udipi et al. | 623/1.42 |
| 2004/0236410 A1* | 11/2004 | Herweck et al. | 623/1.21 |
| 2005/0037052 A1 | 2/2005 | Udipi et al. | |
| 2005/0038134 A1 | 2/2005 | Loomis et al. | |
| 2005/0038497 A1 | 2/2005 | Neuendorf et al. | |
| 2005/0043755 A1* | 2/2005 | Wilson et al. | 606/200 |
| 2005/0043786 A1 | 2/2005 | Chu et al. | |
| 2005/0049693 A1 | 3/2005 | Walker | |
| 2005/0049694 A1 | 3/2005 | Neary | |
| 2005/0054774 A1 | 3/2005 | Kangas | |
| 2005/0055044 A1 | 3/2005 | Kangas | |
| 2005/0055078 A1 | 3/2005 | Campbell | |
| 2005/0060020 A1 | 3/2005 | Jenson | |
| 2005/0064088 A1 | 3/2005 | Fredrickson | |
| 2005/0065501 A1 | 3/2005 | Wallace | |
| 2005/0065545 A1 | 3/2005 | Wallace | |
| 2005/0065593 A1 | 3/2005 | Chu et al. | |
| 2005/0074406 A1 | 4/2005 | Couvillon, Jr. et al. | |
| 2005/0074545 A1 | 4/2005 | Thomas | |
| 2005/0075714 A1 | 4/2005 | Cheng et al. | |
| 2005/0079274 A1 | 4/2005 | Palasis et al. | |
| 2005/0084515 A1 | 4/2005 | Udipi et al. | |
| 2005/0106210 A1 | 5/2005 | Ding et al. | |
| 2005/0113903 A1 | 5/2005 | Rosenthal et al. | |
| 2005/0171596 A1* | 8/2005 | Furst et al. | 623/1.15 |
| 2005/0209680 A1* | 9/2005 | Gale et al. | 623/1.15 |
| 2005/0228473 A1 | 10/2005 | Brown | |
| 2005/0234538 A1* | 10/2005 | Litvack et al. | 623/1.11 |
| 2006/0058868 A1* | 3/2006 | Gale et al. | 623/1.15 |
| 2006/0079955 A1* | 4/2006 | Brown | 623/1.22 |
| 2006/0224237 A1* | 10/2006 | Furst et al. | 623/1.46 |

FOREIGN PATENT DOCUMENTS

| | | |
|---|---|---|
| EP | 0 301 856 | 2/1989 |
| EP | 0 388 234 | 9/1990 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18331 | 4/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/49544 | 6/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/079387 | 9/2005 |

OTHER PUBLICATIONS

Anonymous, *Heparin-coated stents cut complications by 30%*, Clinica 732:17 (Nov. 18, 1996), htto://www dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

(56) References Cited

OTHER PUBLICATIONS

Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Markou et al., *Boundary layer drug delivery using a helical catheter*, J. of Controlled Release 53 281-288 (1998).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Shigeno, *Prevention of Cerebrovascular Spasm by Bosentan, Novel Endothelin Receptor*, Chemical Abstract 125:212307 (1996).
va Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
International Search Report for PCT/US2007/012889 filed May 31, 2007 mailed Nov. 30, 2007, 15 pgs.

* cited by examiner

DRUG DELIVERY SPIRAL COIL CONSTRUCT

FIELD

This invention is directed to a local drug delivery implant. More specifically, the invention is related to a spiral or coil drug delivery construct.

BACKGROUND

Various devices and methods have been proposed for local application of a therapeutic agent or drug such as stents, vascular paving, and particle delivery. Stents are metallic or polymeric implantable structures that have been modified for local delivery of a drug. A polymer dissolved in a solvent including a drug can be applied to the stent. The solvent is removed, leaving behind a polymer coated stent capable of delivering a drug. A disadvantage of using a stent includes the trauma caused to the lumen, such as a blood vessel, during implantation of the stent. Radial pressure applied by the stent can lead to inflammation and tissue damage, which can cause the onset of restenosis or amplify the degree of vascular smooth muscle cell proliferation and migration. Hyper-proliferation and migration of vascular smooth muscle cells caused by the application of radial pressure by a stent can mitigate the effects of local therapeutic substance application.

For some applications such as vulnerable plaque, radial pressure applied by a stent can cause more sever damage than just inducement of restenosis. Unlike occlusive plaques that impede blood flow, vulnerable plaque develops within the arterial walls. Vulnerable plaque can exist without the symptomatic characteristic of a substantially narrow arterial lumen. The intrinsic histological features that may characterize a vulnerable plaque include increased lipid content, increased macrophage, foam cell and T lymphocyte content, and reduced collagen and smooth muscle cell content. This fibroatheroma type of vulnerable plaque is often referred to as "soft" collagen, whose reduced concentration combined with macrophage derived enzyme degradations cause the fibrous cap of these lesions to rupture under unpredictable circumstances. When ruptured, the lipid core contents, thought to include tissue factor, contact the arterial bloodstream, causing a blood clot to form that can completely block the artery resulting in acute coronary syndrome (ACS). This type of atherosclerosis is coined "vulnerable" because of unpredictable tendency of the plaque to rupture. It is thought that hemodynamic and cardiac forces, which yield to circumferential stress, shear stress, and flexation stress, may cause disruption of fibroatheroma type of vulnerable plaque. These forces may arise as the result of simple movements, such as getting out of bed in the morning, in vivo forces related to blood flow and the beating of the heart, as well as radial force applied by a stent. Accordingly, it is desirable to treat conditions such as vulnerable plaque with adequate source of drug delivery without the drawbacks associated with a stent.

Vascular paving can be performed by loading a monomer, pre-polymer or polymer in a balloon catheter, and then applying the composition directly to the inside of a tissue lumen within a zone occluded by the catheter balloon. The application can be through pores of the balloon, for example. The process is followed by curing or polymerizing the applied composition. The tissue surface may be an internal or external surface, and can include the interior of a tissue lumen or hollow space whether naturally occurring or occurring as a result of surgery, percutaneous techniques, trauma or disease. The polymeric material can be reconfigured to form a coating or "paving" layer in intimate and conforming contact with the surface. The resulting paving layer optionally can have a sealing function. The coating preferably has a thickness on the tissue surface on the order of 0.001-1.0 mm; however, coatings having a thickness outside that range may be used as well. By appropriate selection of the material employed and of the configuration of the paving material, the process can be tailored to satisfy a wide variety of biological or clinical situations. Drawbacks associated with vascular paving include the downstream flow and waste of the paving material prior to the curing of the composition and difficult and cumbersome procedural steps for the surgeon including the necessity to occlude the vessel in which the procedure is performed and the curing or polymerization of the polymer to achieve conformal coating about the location where its benefit is most desired. In sum, vascular paving has been considered a difficult procedure which can certainly out weight its benefits.

Particle drug delivery includes release of particles having a drug at the treatment site. If the particles are delivered so as to be embedded within the treatment site, they can cause sever trauma to the vessel, which would present the same issues as a stent as described above. If the particles are simply delivered without being embedded within the lumen, the therapeutic effect of the particles can depend on their size. Too small of particles can simply wash away with blood flow, resulting in negligible therapeutic treatment at the desired site. Moreover, other areas of the body not in need of treatment will be exposed to the drug, which in effect would be equivalent to systemic delivery of the drug. If the particles are too large, they form an embolus, causing cell damage or death.

It is desirable to address and treat vascular conditions, such as vulnerable plaque, a disease that is often seen in diabetics, with a use of a device that does not provide the above described drawbacks. It is also desirable to have a device which provides a sustained delivery of therapeutic agents to long or extended portions of coronary vessels or to a multitude of focal manifestations of a disease site. The use of the implantable device of the present invention, as can be appreciated by one having ordinary skill in the art, is certainly not limited to coronary vessels as it can have a multitude of applications in a variety of biological lumens and cavities.

SUMMARY

In accordance with one aspect of the present invention, an implantable medical device is provided for the treatment of various disorders including vascular disorders. The implant comprises a helical construct including a set of spiral coils for local in vivo application of a therapeutic substance in a biological lumen. The construct is intended to conform against the lumen or cavity wall but to apply minimum force or pressure against the wall. In some embodiments, minimum force is defined as less force as applied by any commonly used balloon expandable or self-expandable stent or a stent-graft. In some embodiments, the construct is not intended to maintain patency of the vessel, but only to provide a means for delivery of a drug. In some embodiment, the helical construct is configured to apply less than 0.75 Bar of pressure to the biological lumen. In some embodiments, the construct can have a coil pitch from about 0.5 mm to about 10 mm. The coil pitch can be constant or variable along the length of the device. In some embodiments, a proximal or distal segment of the helical construct can have a coil pitch that is different than a middle segment of the construct. In some embodiments, the helical construct has a coil contact angle of 0 to 80 degrees against the biological lumen. In some embodiments, it can be between 10 to 70 degrees.

In some embodiments, the helical construct includes a first set and a second set of spiral coils such that the first set of spiral coils has a counter helical configuration or direction to the second set of spiral coils (i.e., opposing "helicity"). The first set of spiral coils can be connected to the second set of spiral coils by a V-shaped or U-shaped connector. They can also be connected by a polymeric connector. The connector can be biodegradable.

The helical construct can be made from a polymeric material, a metallic material or a combination of polymers and/or metals. The helical construct can be biodegradable. The therapeutic substance can be mixed, embedded, or blended in the body of the construct or can be coated on the construct.

In accordance with another aspect, a method of treating a disorder, such as a vascular disorder, is provided. The method comprises inserting or implanting the helical construct at a target location within a patient such as a mammalian or human subject. The disorder can be vulnerable plaque or restenosis. The device can be used in any body cavity, lumen or blood vessel, including the urethra, peripheral blood vessels, lower or upper gastric intestinal structures and the like.

BRIEF DESCRIPTION

DETAILED DESCRIPTION

Figure 1:
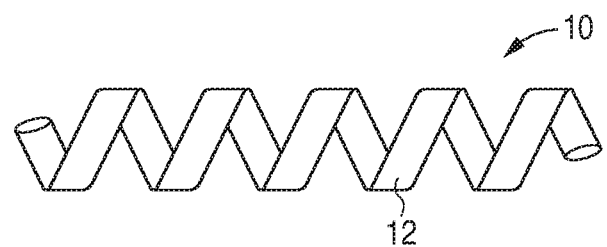
FIG. 1 illustrates a spiral or helical drug delivery construct according to one embodiment of the invention.
Figure 2:
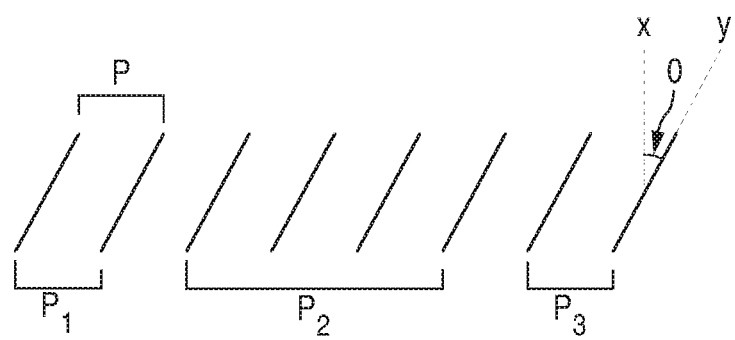
FIG. 2 is a schematic side elevation view of the construct of FIG. 1 depicting coil pitch and coil contact angle.

FIG. 1 illustrates a helical drug delivery construct 10 having a coil body 12 in a spiral configuration. The construct 10 can include a drug or therapeutic substance, terms which can be used interchangeably, in the body of the construct itself or on a coating (not illustrated) deposited on a surface of the construct 10. The construct 10 is intended to conform against a lumen or cavity wall but to apply minimum force or pressure against the wall. In some embodiments, minimum force is defined as less force as applied by a balloon expandable or self-expandable stent or a stent-graft used in the U.S. or European market. In some embodiments, the construct 10 is not intended to maintain patency of the vessel, but only to provide a means for drug delivery. In one embodiment, the force or pressure applied to the lumen wall during and post deployment is less than 0.75 Bar (10.88 psi or about 11 psi) as measured by the application of pressure by the total surface area of contact. In one preferred embodiment, the pressure applied by spiral or helical construct 10 is less than 0.5 Bar (7.25 psi). In some embodiments, the applied pressure can be less than: 0.25 Bar (3.62 psi), 0.2 Bar (2.9 psi), 0.1 Bar (1.45 psi), 0.05 Bar (0.725 psi), 0.01 Bar (0.145 psi), 0.001 Bar (0.014 psi), or 0.0001 Bar (0.00145 psi). In some embodiments, it has to be at least slightly above 0 Bar so that the spiral or helical coil structure is at least maintained in the exact vicinity or general vicinity of implantation such that there is little to no post-movement of the construct 10 subsequent to the retraction of the catheter which delivers the construct 10. Accordingly, spiral or helical construct 10 does not inflict trauma on the lumen wall which may cause inflammation and hyper-proliferation and migration of vascular smooth muscle cells. Moreover, for vulnerable plaque application, spiral or helical construct 10 provides for a drug delivery means while minimizing the risk of causing plaque rupture. In some embodiments application of an inwardly radial pressure of over 0.75 Bar can cause inward compression or collapse of the construct 10. In some embodiments, the radial pressure of greater than 0.5 Bar can cause radial collapse of the construct 10. Yet in some embodiments the radial pressure of great than 0.25, 0.2, 0.1, 0.05, 0.01, 0.001, or 0.0001 Bar can cause the collapse or inward compression of the construct 10. As indicative of these forces, construct 10 is soft, pliable, easily collapsible and compressible. The overall length of the construct 10 can be from 10 mm to 300 mm. In some embodiments, it must be at least 40 mm. In some embodiments the length should not exceed 200 mm or alternatively 100 mm. This extended length provides an elongated source of drug delivery with a flexible and conformal platform that allows for navigation through tortuous vascular structure which otherwise would be unachievable with the use of common stents. The inner diameter of the spiral or helical construct 10 can range from 1 mm to 50 mm—as measured in its natural state. The cross-section of the coil 12 can be circular, oval, or in a "ribbon" form. The coil pitch P, as illustrated in FIG. 2, or the distance between individual coils 12 or helical turns of the coil 12 can be consistent throughout the body or variable, such as along a segment of the body. The coil pitch P is measured at the construct's natural or "undisturbed" state, with no application of pressure or force so as to vary the length of the construct 10. Variability in the coil pitch can allow for areas where a greater amount or concentration of drug is released. In some embodiments, coil pitch P can be from 0.15 mm to 10 mm. In some embodiment, it can be from 1 mm to 5 mm. In some embodiments helical construct 10 can have pitches $P_1$, $P_2$ and $P_3$ at the proximal, middle and distal segments thereof such that: $P_1=P_3$; $P_1>P_2$; $P_1>P_3$; $P_3>P_1$; and/or $P_3>P_2$. In some embodiments, pitch variation can be $P_2>P_1$ and/or $P_2>P_3$. It should be noted that proximal and distal segments include at least two coils, the remaining coils defining the middle segment.

Individual coils 12 can have a coil contact angle Φ with a lumen wall in a range from 0 degrees (coils being perpendicular to the lumen wall) to 80 degrees (coils being almost parallel to the lumen wall). In some embodiments, the contact angle can be 10 degrees to 70 degrees; 20 degrees to 60 degrees; and 30 degrees to 50 degrees. It should be noted that axis x is normal to the issue wall and axis y is along the coil, as best illustrated by FIG. 2.

Figure 3:
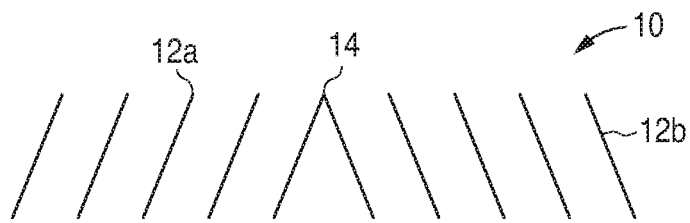
FIG. 3 illustrates a spiral or helical drug delivery construct according to another embodiment of the invention.

In one embodiment, as illustrated by FIG. 3, helical construct 10 can include at least two coil segments 12a and 12b having opposing helical configuration. The two coil segments 12a and 12b can be joined by any means including a V- or U-shaped connector 14, a polymeric coupler or the like. The coils and connector 14 can be made from a single, uniform piece or the connector can be a separate segment, joint to the coils by an adhesive or the like. The connector can be biodegradable. The coil segments 12a and 12b can have the same general shape including pitch and contact angle. In some embodiments, the pitch and contact angle of one segment 12a and be different that the other segment 12b. Moreover, each segment 12a and 12b can have its own individual pitch and contact angle pattern, such as a variable pitch pattern along a designated segment thereof. Coil segments 12a and 12b can be made from the same material or different materials and can include the same drug or different drugs. In some embodiments, each can include a different amount of the same drug. Upon deployment, compressed coil segments 12a and 12b can "uncoil" inopposite directions in the lumen or cavity of the patient. The "right-handed" and "left-handed" corkscrew configuration is advantageous in that each spiral coil segment 12a and 12b acts to counter-balance the rotation of the coil of the other. Less rotational motion can lead to reduction in trauma or injury to the vessel wall during deployment and a more controlled delivery of the implantable medical device. It should also be appreciated that the construct of the present invention can include three coil segments such that the middle coil segment has a different helical configuration or opposing rotation than the end coil segments. The lengths of the end coils segments can be less than the middle coil segment and provide for counter balance of the rotational expansion of the middle segment upon deployment.

The helical construct 10 can be made from a biodegradable polymer, biostable polymer, a metallic material or a combination of such material. Biostable refers to polymers that are not biodegradable. The terms biodegradable, bioabsorbable, and bioerodable are used interchangeably and refer to materials that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes. The construct 10 can also be made from biodegradable metals (e.g., magnesium, iron, tungsten, or ferrous oxide), alone or in combination with other metals and polymers. In one embodiment, the construct 10 can be a combination of biodegradable metal(s) with biodegradable polymer(s). The metal can form the core with a polymer shell enclosing the core. The metal and the polymer can be blended or layered as well. The metal can be distributed in particle form in the polymer.

The construct 10 can be made from a soft, flexible filament including monofilaments or braided string filaments. The construct 10 can be a continuous wire or a wire having connections. The construct 10 can be an extruded polymer tube. In some embodiment, the construct 10 can be fabricated as a polymer matrix loaded, embedded or blended with a drug or therapeutic agent. The construct 10 may have drug-loaded micro- or nano-particles embedded within the body of the construct 10 or coated on the construct 10. The particles may include metallic material such as alkaline earth metals (magnesium) or transition metals (gold) having a coating of the drug with or without a polymeric material. In some embodiments the particles may be fullerenes including a drug, with or without metallic or polymeric components. In some embodiments, the particles can be ceramic or bioglass. The particles can be micelles (e.g., polymer micelles), liposomes, polyliposomes, polymerosomes, or membrane vesicles with a membrane that includes a polymerosomes, as is well understood by one of ordinary skill in the art. In one embodiment, the micro- or nano-particles are spherical or quasi-spherical formed of a polymer encapsulating the drug. When the device is in contact with body fluids, the polymer can swell and/or hydrolyze, thus releasing the drug.

The construct 10 may include a coating on its surface of a pure drug, such a heparin, or a drug with a polymeric carrier.

Representative examples of polymers that may be used to fabricate the construct 10 include, but are not limited to, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly (caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The drug or therapeutic agent includes agents that have anti-proliferative or anti-inflammatory properties or can have other properties such as antineoplastic, antiplatelet, anti-coagulant, anti-fibrin, antithrombogenic, antimitotic, antibiotic, antiallergic, antifibrotic, and antioxidant. The agents can be cystostatic agents, agents that promote the healing of the endothelium such as NO releasing or generating agents, agents that attract endothelial progenitor cells, agents that promote the attachment, migration or proliferation of endothelial cells (e.g., natriuretic peptides such as CNP, ANP or BNP peptide or an RGD or cRGD peptide), while impeding smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides, small interfering RNA (siRNA), small hairpin RNA (shRNA), aptamers, ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy)propyl-rapamycin, 40-O-[2-(2-hydroxy)ethoxy] ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, mometasone, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, SIKVAV peptides, elevating agents such as cANP or cGMP peptides, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

Construct 10 can further include or be made from a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the device by being non-fouling, hemocompatible, actively non-thrombogenic, or anti-inflammatory, all without depending on the release of a pharmaceutically active agent. Representative biobeneficial materials include, but are not limited to, polyethers such as poly(ethylene glycol), copoly(ether-esters) (e.g. PEO/PLA), polyalkylene oxides such as poly(ethylene oxide), poly (propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof.

In some embodiments, the construct 10 may be made from or to include shape memory polymers or metals. Most polymers exhibit some shape memory when deformed and stored at a temperature below $T_g$. The best shape memory polymers have light cross-linking or crystalline domains that serve to fix the locations of the polymeric chains. After a polymer is deformed and kept at a temperature below $T_g$, the polymer chains are in a non-equilibrium extended conformation. Upon heating above $T_g$, the polymer chains have sufficient mobility to return to their desired lower-energy "coiled" conformation. The cross-links or crystalline domains serve to prevent the migration of portions of the polymer chains, and thus the gross structure is forced to return to its original shape. Representative examples of a shape memory polymers include, but are not limited to, copolymers of poly(caprolactone) and poly(L-lactide-co-trimethylene carbonate). A representative example of a shape memory metal includes Nitinol.

The construct 10 may also include a binder or a plasticizer for changing the properties of the device. Plasticizers can be added, for example, to reduce crystallinity, lower the glass-transition temperature ($T_g$), or reduce the intermolecular forces between polymers. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading.

Examples of plasticizing agents include, but are not limited to, low molecular weight polymers (such as single-block polymers, multi-block copolymers, and other copolymers such as graft copolymers), oligomers (such as ethyl-terminated oligomers of lactic acid), small organic molecules, hydrogen bond forming organic compounds with and without hydroxyl groups, polyols (such as low molecular weight polyols having aliphatic hydroxyls), alkanols (such as butanols, pentanols and hexanols), sugar alcohols and anhydrides of sugar alcohols, polyethers (such as poly (alkylene glycols)), esters (such as citrates, phthalates, sebacates and adipates), polyesters, aliphatic acids, proteins (such as animal proteins and vegetable proteins), oils (such as, for example, the vegetable oils and animal oils), silicones, acetylated monoglycerides, amides, acetamides, sulfoxides, sulfones, pyrrolidones oxa acids, diglycolic acids, and any analogs, derivatives, copolymers and combinations of the foregoing.

Figure 4:
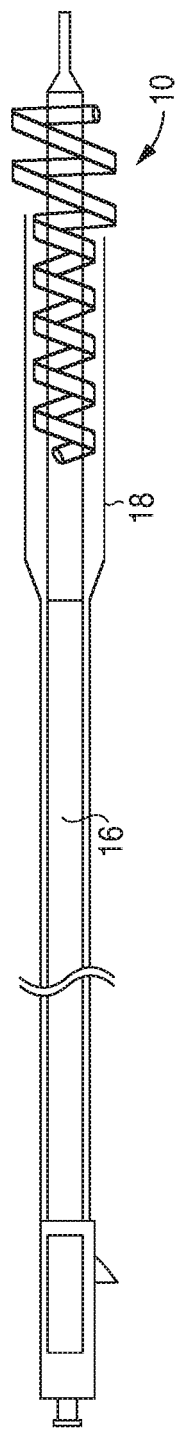
FIGS. 4 and 5 illustrate various delivery techniques in accordance with embodiments of the invention.
Figure 5:
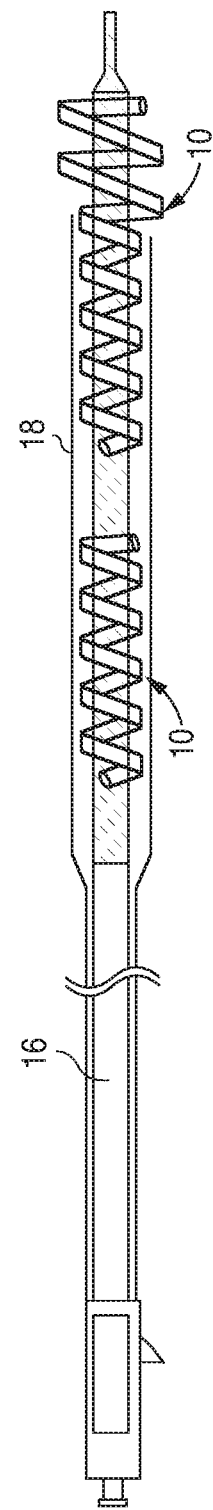

FIG. 4 depicts spiral construct 10 supported on a catheter assembly 16. A retractable sheath 18 is being drawn back allowing the spiral construct 10 to self-expand for implantation (i.e., the construct is a self-expandable construct). In some embodiment, spiral construct 10 can be balloon expandable such that application of radial pressure causes the radial expansion of the coils 12. FIG. 5 is similar to FIG.

4 but depicts two spiral constructs 10 being delivered in tandem. Thus, many diseased areas can be treated with one procedure rather than many separate procedures. Navigation of such catheter systems, including use of guidewires, is well known in the art. The spiral construct 10 may be crimped in a manner that segments of the coil 12 may overlap, particularly for the "ribbon" shaped coils so as to reduce the length of the delivered construct 10. However, reduction of the length of the construct 10 for delivery may counterbalance flexibility that is required to navigate the device through tortuous paths.

The construct 10 of the present invention may be delivered with a viscous solution containing a biologically benign matrix and therapeutics for regional therapy of the target vessel. Examples include, but are not limited to, hyaluronic acid or carboxymethyl cellulose, or PVP, suspended with PEA nano-particles containing everolimus. This type of solution may act as a lubricant for smooth delivery of the device and may also start biological therapy at the start of deployment. The viscous solution may be placed on the devices, generally within the sheath or on the outside of the sheath. The solution can also be applied or injected by the catheter. Application of compositions with catheters is well known in the art.

In some embodiments, the viscous solution, as mentioned above, may contain an ampiphilic, surface active molecule to plasticize the device for both mechanical properties and therapeutic release modulation. Examples include PLURONIC and 2-methacryloyloxyethyl phosphorylcholine-co-lauryl methacrylate (MPC-co-LMA). The plasticizer can suppress the $T_g$ to make the polymer or polymeric matrix pliable and flexible. The viscous solution of this embodiment may be applied to devices made from shape memory polymers discussed previously. The addition of the viscous solution to the delivery system may allow for increased conformation of the device to the vessel wall and an increase in biological therapy associated with the treatment needed at the site of deployment. In some embodiment, the viscous solution should have a viscosity of not less than 5 centipoise at room temperature. In some embodiments, the viscosity is not less than 10 centipoise at room temperature.

The construct 10 of the present invention can be preferably used for the treatment of vascular conditions such as restenosis and vulnerable plaque. In some embodiment, the construct 12 is used for regional therapy which requires sustained delivery of drug or therapeutic agents to long portions of coronary vessels, or alternatively to a multitude of focal manifestations of a diseased condition.

Constructs or scaffoldings having other geometrical shapes can also be included within the scope of the present invention. For example, the construct can be made from a series of joined V or U shaped struts or elements that are rolled into a cylindrical configuration around the axis orthogonal to the plane of the Vs or Us. Tightly wound in this configuration, the construct can be delivered to the target site where it is deployed through unwinding. Additionally, THE scaffolding or construct can be made including hollow bodies such that a hydrogel and/or drug can be included in the hollow body.

While particular embodiments of the present invention have been shown and described, it will be obvious to those skilled in the art that changes and modifications can be made without departing from this invention in its broader aspects. For example, absorptive material such as dyes can be doped into the construct 10 for allowing heat or UV modification of the mechanical properties of the construct 10. Accordingly, the claims are to encompass all such changes and modifications.

What is claimed is:

1. An implantable medical device, comprising: a helical construct including a spiral coil and a therapeutic substance for local in vivo application of the therapeutic substance in a biological lumen, wherein the helical construct is configured to apply less than 0.75 Bar of pressure to a wall of the biological lumen when the helical construct is deployed in the biological lumen and after the helical construct is deployed and implanted in the biological lumen, wherein the helical construct is in an expanded configuration, from a reduced configuration, and configured to be in contact with the wall of the biological lumen post deployment and when implanted in the biological lumen, and wherein the helical construct includes a proximal free end and a distal free end, both ends which are configured to be positioned in the biological lumen when the helical construct is expanded and implanted.

2. The implantable medical device of claim 1 wherein the pressure is less than 0.5 Bar.

3. The implantable medical device of claim 1 wherein the pressure is less than 0.25 Bar.

4. The implantable medical device of claim 1 wherein the pressure is less than 0.2 Bar.

5. The implantable medical device of claim 1 wherein the pressure is less than 0.1 Bar.

6. The implantable medical device of claim 1 wherein a coil pitch of the helical construct is from about 0.15 mm to about 10 mm.

7. The implantable medical device of claim 1 wherein the helical construct has a variable coil pitch.

8. The implantable medical device of claim 1 wherein the helical construct comprises a proximal segment, a distal segment, and a middle segment there between, and wherein a coil pitch of the proximal segment is different than a coil pitch of the middle segment and/or a coil pitch of the distal segment is different than a coil pitch of the middle segment.

9. The implantable medical device of claim 8 wherein the coil pitch of the proximal segment or distal segment is greater than the coil pitch of the middle segment.

10. The implantable medical device of claim 1 wherein the helical construct is shaped to have a coil contact angle of 0 to 80 degrees.

11. The implantable medical device of claim 1 wherein the helical construct is shaped to have a coil contact angle of 10 to 70 degrees.

12. The implantable medical device of claim 1 wherein the helical construct includes a first set and a second set of spiral coils such that the first set of spiral coils has a counter helical configuration than the second set of spiral coils.

13. The implantable medical device of claim 12 wherein the first set of spiral coils is connected to the second set of spiral coils by a V-shaped or U-shaped connector.

14. The implantable medical device of claim 12 wherein the first set of spiral coils is connected to the second set of spiral coils with a polymeric connector.

15. The implantable medical device of claim 12 wherein the first set of spiral coils is connected to the second set of spiral coils with a biodegradable connector.

16. The implantable medical device of claim 12 wherein the device includes two different therapeutic substances such that the first set of spiral coils carries a first therapeutic substance and the second set of spiral coils carries a second therapeutic substance.

17. The implantable medical device of claim 12 wherein the first set of spiral coils is made of a different material than the second set of spiral coils.

18. The implantable medical device of claim 12 wherein the first set of spiral coils carries a different amount of the therapeutic substance than the second set of spiral coils.

19. The implantable medical device of claim 1 wherein the helical construct is made from a polymeric material.

20. The implantable medical device of claim 1 wherein the helical construct is made from a biodegradable polymeric material.

21. The implantable medical device of claim 1 wherein the helical construct is made from a biodegradable polymeric material and a bioerodable metallic material.

22. The implantable medical device of claim 1 wherein the therapeutic substance is embedded within or coated on the helical construct.

23. The implantable medical device of claim 1 wherein the length of the helical construct is at least 40 mm.

24. The implantable medical device of claim 1 wherein the helical construct is self-expandable.

25. The implantable medical device of claim 1 wherein the helical construct comprises a first end segment, a second end segment and a middle segment there between, such that the first end segment has a coil pitch that is greater than the second end segment.

26. The implantable medical device of claim 1 wherein the helical construct is shaped to have a coil angle of 20 to 60 degrees.

27. The implantable medical device of claim 1 wherein the helical construct comprises a proximal coil segment, a distal coil segment, and a middle coil segment there between, and wherein the middle coil segment has a counter helical configuration than both the proximal and distal coil segments.

28. The implantable medical device of claim 27 wherein the length of each of the proximal and distal coil segments is less than the length of the middle coil segment.

29. The implantable medical device of claim 1 wherein the helical construct is made of a metallic material.

30. The implantable medical device of claim 1 wherein the helical construct is made of a biodegradable metallic material.

31. The implantable medical device of claim 1 wherein the helical construct includes a metallic core with a polymer shell enclosing the core.

32. The implantable medical device of claim 1 wherein the helical construct comprises a polymer having metallic particles.

33. The implantable medical device of claim 1 further comprising micro- or nano-particles, embedded within the helical construct or coated on the helical construct, the micro- or nano-particles carrying the therapeutic substance for in vivo delivery.

34. The implantable medical device of claim 1 wherein the therapeutic substance is rapamycin, 40-O-(2-hydroxy) ethyl-rapamycin (everolimus), 40-epi-(N1-tetrazolyl)-rapamycin, 40-O-(3-hydroxy)propyl-rapamycin, 40-O-[2-(2-hydroxy)ethoxy]ethyl-rapamycin, 40-O-tetrazole-rapamycin, paclitaxel or docetaxel.

35. The implantable medical device of claim 1 wherein the helical construct comprises a shape memory material.

36. The implantable medical device of claim 1 additionally including a delivery catheter on which the helical construct is crimped such that segments of the coil overlap one another when the construct is in a crimped configuration on the catheter.

37. A method of treating a vascular disorder comprising implanting the device of claim 1 in a human patient, such that the device of claim 1 applies less than 0.75 Bar of pressure on to the wall of the biological lumen when implanted in the expanded configuration and in contact with the wall of the biological lumen, wherein implanting is by a delivery device such that the device of claim 1 is left behind in the biological lumen after withdrawal of the delivery device.

38. The method of claim 37 wherein the disorder is vulnerable plaque.

39. The method of claim 37 wherein the disorder is restenosis.

40. The method of claim 37 wherein the device does not maintain patency of a vessel in which the device is implanted.

41. The method of claim 37 wherein post implantation, the device is maintained in an exact vicinity or a general vicinity of a site of implantation with little to no post implantation movement of the device for a selected duration of time for the application of a quantity of the therapeutic substance.

42. The method of claim 37 wherein the device does not inflict trauma on a lumen wall at a site of implantation.

43. The method of claim 37 wherein the device does not cause hyper-proliferation and migration of vascular smooth muscle cells at a site of implantation.

44. The method of claim 37 additionally comprising delivering a viscous solution containing a biologically benign matrix and a therapeutic agent to a site of implantation.

45. The method of claim 44 wherein the viscous solution acts as a lubricant for smooth delivery of the helical construct and provides for biological therapy to the site of implantation of the helical construct.

46. The method of claim 37 additionally comprising delivering a solution including an amphiphilic, surface active molecule to a site of implantation to change a mechanical property of a material from which the helical construct is made.

47. The method of claim 37 additionally comprising delivering a solution to a site of implantation for increasing conformation of the helical construct to a vessel wall in contact with the helical construct.

48. The method of claim 37 additionally comprising delivering a solution to a site of implantation for changing a property of a material from which the helical construct is made or changing a release profile of the therapeutic substance, wherein the solution has a viscosity not less than 5 centipoise.

49. The method of claim 48 wherein the viscosity is not less than 10 centipoise.

* * * * *